(12) United States Patent
Otts et al.

(10) Patent No.: US 10,358,277 B2
(45) Date of Patent: Jul. 23, 2019

(54) STORAGE SYSTEM AND METHOD FOR STORING MATERIAL

(71) Applicant: Beckman Coulter, Inc., Brea, CA (US)

(72) Inventors: Stephen Otts, Fishers, IN (US); Stefan Rückl, Garching bei Munchen (DE)

(73) Assignee: Beckman Coulter, Inc., Brea, CA (US)

( * ) Notice: Subject to any disclaimer, the term of this patent is extended or adjusted under 35 U.S.C. 154(b) by 91 days.

(21) Appl. No.: 15/418,003

(22) Filed: Jan. 27, 2017

(65) Prior Publication Data

US 2017/0217663 A1    Aug. 3, 2017

(30) Foreign Application Priority Data

Jan. 29, 2016 (EP) .................................... 16000223

(51) Int. Cl.

| | | |
|---|---|---|
| *B65D 83/04* | (2006.01) | |
| *A47B 88/969* | (2017.01) | |
| *B65D 43/20* | (2006.01) | |
| *B65D 47/28* | (2006.01) | |
| *B65D 90/60* | (2006.01) | |
| *A47B 88/40* | (2017.01) | |
| *B65G 69/04* | (2006.01) | |
| *G01N 35/04* | (2006.01) | |

(52) U.S. Cl.
CPC ........ *B65D 83/0481* (2013.01); *A47B 88/969* (2017.01); *B65D 43/20* (2013.01); *B65D 47/286* (2013.01); *B65D 90/60* (2013.01); *A47B 2088/4015* (2017.01); *A47B 2210/07* (2013.01); *B65G 69/0441* (2013.01); *G01N 35/04* (2013.01); *G01N 2035/0405* (2013.01)

(58) Field of Classification Search
CPC .......... A47B 88/969; A47B 2088/4015; A47B 2210/03; A47B 2210/07; B65D 43/20; B65D 47/286; B65D 83/0481; B65D 90/587; B65D 90/60
USPC .......................... 312/301, 310; 414/185, 414
See application file for complete search history.

(56) References Cited

U.S. PATENT DOCUMENTS

| | | | | |
|---|---|---|---|---|
| 777,421 | A * | 12/1904 | Keller et al. .............. | F27B 1/20 414/185 |
| 875,571 | A * | 12/1907 | Ernst ......................... | F27B 1/20 414/185 |

(Continued)

FOREIGN PATENT DOCUMENTS

| | | | | |
|---|---|---|---|---|
| FR | 2938166 A1 | * | 5/2010 | .......... E05C 19/166 |
| JP | 2002-251670 A | | 9/2002 | |
| JP | 2003-083987 A | | 3/2003 | |

OTHER PUBLICATIONS

European Search Repot dated Jul. 14, 2016 for EP Application No. 1600223.4, 10 pages.

*Primary Examiner* — James Keenan
(74) *Attorney, Agent, or Firm* — Kilpatrick Townsend & Stockton LLP

(57) ABSTRACT

A storage system for storing material such as sample tube caps comprises a drawer with a reservoir, the drawer being movable between a first position and a second position. A storage container is arranged below the reservoir of the drawer when the drawer is arranged in the first position. A transport device is configured to retrieve material from the storage container and to transport the material out of the storage container. Therein, the reservoir of the drawer comprises a bottom with at least one closable opening.

20 Claims, 3 Drawing Sheets

(56) References Cited

U.S. PATENT DOCUMENTS

| | | | | |
|---|---|---|---|---|
| 885,920 A | * | 4/1908 | Goldey | F27B 1/20 |
| | | | | 414/185 |
| 1,553,694 A | | 9/1925 | Johnson et al. | |
| 2,211,956 A | * | 8/1940 | MacMichael | F27D 3/0025 |
| | | | | 414/185 |
| 2,690,870 A | | 10/1954 | Harman | |
| 3,397,654 A | * | 8/1968 | Snyder | B61D 7/20 |
| | | | | 105/305 |
| 3,683,826 A | * | 8/1972 | Rieckmann | E05G 5/006 |
| | | | | 109/46 |
| 3,883,017 A | * | 5/1975 | Shirai | A24C 5/356 |
| | | | | 414/403 |
| 4,403,908 A | * | 9/1983 | Cartoceti | B65G 65/32 |
| | | | | 414/403 |
| 4,500,246 A | * | 2/1985 | Janisiewicz | H05K 13/021 |
| | | | | 221/11 |
| 5,482,423 A | * | 1/1996 | Tawara | B65G 1/08 |
| | | | | 220/529 |
| 5,588,792 A | * | 12/1996 | Tiso | B01L 9/543 |
| | | | | 221/221 |
| 2003/0047418 A1 | * | 3/2003 | Okada | B65G 47/1471 |
| | | | | 198/459.1 |
| 2009/0118860 A9 | * | 5/2009 | Sjostrom | G07D 1/02 |
| | | | | 700/231 |
| 2014/0054287 A1 | * | 2/2014 | Kitazawa | B65D 21/02 |
| | | | | 220/23.87 |

\* cited by examiner

STORAGE SYSTEM AND METHOD FOR STORING MATERIAL

CROSS REFERENCE TO RELATED APPLICATIONS

This application claims priority to EP Patent Application No. 16000223.4, filed on Jan. 29, 2016 entitled "Storage System and Method for Storing Material," the contents of which are herein incorporated by reference.

The invention relates to a storage system and to a method for storing material such as sample tube caps.

Storage systems are used in automated systems like automated analysing systems to store consumable material such as sample tube caps. In such automatic systems, the pieces of the consumable material such as sample tube caps are continuously required by and withdrawn from the storage system.

In an automated sample tube analysing system, the content of sample tubes is analysed. Multiple sample tubes are transported through the analysing system by, e.g., robotic arms or conveyors. Prior to the analysing process, the sample tubes may be opened via a decapper, so a sample can be drawn from the open sample tubes e.g. via a probe. Open sample tubes may be closed with sample tube caps at a recapping position of the analysing system, e.g. for storage purpose. At the recapping position, a steady supply of sample tube caps is required.

To provide such a steady supply of sample tube caps, a plurality of sample tube caps is stored in a closed storage container of a storage system. A transport device such as a conveyor is configured to retrieve sample tube caps from the storage container and to transport the sample tube caps out of the storage container to present them for pick-up to, e.g., a robot that closes sample tubes. As long as the storage container is substantially filled with sample tube caps, the transport device may provide a steady supply of sample tube caps to the robot. However, it is a problem to refill the closed storage container without interrupting the transport of sample tube caps from within the storage container, which might lead to an interruption of the sample tube analysing system.

In known storage supply systems, the storage container is decoupled from the transportation device, removed from the storage system, refilled, and then moved back into the storage system where it can be coupled to the transport device again.

Furthermore, when the storage container is nearly emptied of the sample tube caps, the remaining sample tube caps are usually arranged in an area within the storage container distant from the transport device. Therefore, even though some sample tube caps still remain in the storage container, the transport device might not be able to provide a steady supply of further sample tube caps.

A problem relates to providing an improved storage system for storing material such as sample tube caps overcoming at least one of the problems indicated above. In particular, a problem may relate to enabling refilling a storage container without interrupting an automatic process and/or enabling an improved distribution of material such as sample tube caps within a storage container of a storage system.

The problem is solved by the subject-matter of the independent claims. Preferred embodiments are the subject-matter of the dependent claims.

An aspect relates to a storage system for storing material such as sample tube caps. The storage system comprises a drawer comprising a reservoir, the drawer being movable between a first position and a second position. The storage container is arranged below the reservoir of the drawer when the drawer is arranged in the first position. A transport device is configured to retrieve material from the storage container and to transport the material out of the storage container. Therein, the reservoir of the drawer comprises a bottom with at least one closable opening.

The storage system is configured to store material such as sample tube caps. In other words, the storage system is designed to store consumable material that is consumed and/or required in an automated process. For example, the storage system may be provided as a push cap feeder, wherein the material may be provided as a plurality of sample tube caps required in a recapper module of a sample tube analysing system. Alternatively, the storage system may be provided as a secondary tube feeder, wherein the material may be provided as a plurality of secondary tubes required for an aliquotation module of the sample tube analysing system. The storage system may be provided and designed as a storage system of the kind described above.

The material may be stored in the storage container of the storage system. The transport device may be provided as conveyor and/or conveyor belt. The transport device may be coupled to the storage container. The transport device retrieves material from the storage container and transports the material out of the storage container to an access point where the transport device presents the material to, e.g., a robot that further processes the material. To enable this transportation of the material, the transport device has access to the inside of the storage container and connects the inside of the storage container to the access point which is arranged outside of the storage container. In particular, the transport device may have access to an area arranged at the bottom of the storage container.

The drawer is arranged above the storage container. The drawer may be closed in the first position wherein the reservoir of the drawer is arranged above the storage container. In this first, e.g., closed position of the drawer, the drawer may cover the storage container from above. Therefore, the storage container may be protected from pollution and/or from collecting dust by the drawer forming a "roof" of the storage container.

In the context of this invention, the terms "below", "above", "up", "down", etc. are terms identifying directions in the reference system of the Earth.

The drawer may be moved from the first position into the second position and vice versa. The second position may be an extended position of the drawer, wherein the drawer is extending out of the storage container. The drawer may be fully or partly extended out of the storage container in the second position. The drawer comprises a reservoir (i.e. a receptacle) as do most known drawers. The reservoir may be substantially box-shaped and may be provided as space between a bottom and, e.g., four lateral walls of the drawer. In the second, e.g., extended position of the drawer, the reservoir of the drawer may be refilled with additional material. Afterwards, the drawer may be moved back from the second position in the first position, wherein the filled reservoir is arranged above the storage container. When the refilled reservoir of the drawer is arranged above the storage container, the at least one closable opening may be opened, thereby releasing the refilled material from the reservoir of the drawer into the storage container. Thereby, the storage container is refilled without the need to decouple it from the transport device, in particular without interrupting and/or stopping the transport device. The transport device may be configured to keep working independently of the position of the drawer. For example the transport device may transport material from the storage container to a location outside of the storage container, where the material is accessible for further processing, e.g. for separating or for adjusting the orientation of individual pieces of material. The transport device may transport material upwards, e.g. laterally past the first position of the drawer, to a position above the drawer. In another embodiment, the transport device may be configured to transport the material through a lateral opening in one of the lateral walls of the storage container.

The closable opening in the bottom of the drawer may be opened and closed. The state of the closable opening may be controlled by controller. Furthermore, the state of the closable opening may also be controlled automatically and/or depend on the position of the drawer.

To enable uninhibited refilling of the storage container, a free space is provided below the first position of the drawer to enable a free fall of the material out of the reservoir through the closable opening and into the storage container.

The storage container is configured to hold a plurality of pieces of the material such as sample tube caps. Furthermore, the storage container may comprise a bottom and lateral walls to hold the material. The storage container requires no additional cover, since the drawer may cover the storage container in its first position. The storage container may be configured to store at least 100 pieces of the material, preferably at least 1000 pieces of the material.

The reservoir of the drawer may be configured to hold at least 10 pieces of the material, preferably at least 50 pieces of the material. The closable opening in the bottom of the drawer is larger than one piece of the material. Preferably, the opening is at least twice as large in any direction as a longest extension of a piece of the material. Thereby, an easy penetrating of the closable opening is enabled and a clogging of the closable opening might be prevented.

According to an embodiment, when the drawer is arranged in the first position, the at least one closable opening is open so that material drops from the reservoir into the storage container. The drawer may be configured so that the closable opening is always substantially open when the drawer is arranged in the first position. In this embodiment, the state of the closable opening depends on the position of the drawer. In this embodiment, the closable opening automatically opens when the drawer is moved into the first position, e.g. from the second position. Thus, a further handling by a user might not be required to open the closable opening. The position of the drawer alone may ensure that the material is released into the storage container. In the open state of the closable opening, gravity ensures that the material drops from the reservoir into the storage container.

According to an embodiment, when the drawer is arranged in the second position, the at least one closable opening is closed so that the reservoir is configured to receive further material. In the second position of the drawer, the closable opening may always be closed. In this embodiment, the closable opening is automatically closed when the drawer is moved into the second position, e.g. from the first position. Thus, a further handling by a user might not be required to close the closable opening. The closed state of the closable opening ensures that the reservoir of the drawer may receive further material without dropping it through the closable opening.

The opening and/or the closing of the closable opening may occur mechanically, magnetically, and/or via electrical control.

According to an embodiment, the bottom of the reservoir comprises a plurality of closable openings which are jointly operable in that
   the plurality of closable openings are jointly opened when the drawer is moved from the second position into the first position and
   the plurality of closable openings are jointly closed when the drawer is moved from the first position into the second position.

The plurality of closable openings provides an improved functionality of the drawer to enable easier refilling of the storage container. All closable openings are jointly operable. In particular, when the drawer is arranged in the second, e.g., extended position, all closable openings are jointly closed. Thus, the reservoir of the drawer may receive additional pieces of the material. When the drawer is moved back into the storage system and back into its first position, the openings are jointly and/or simultaneously opened to release the material from the drawer into the storage container. In this context, the term "jointly" may include the term "simultaneously". To enable the joint operation of the closable openings, all of the closed openings may be mechanically connected to each other via a joining means, e.g. a slidable element.

According to a further development of this embodiment, the closable openings are substantially evenly distributed at the bottom of the reservoir of the drawer. The even distribution enables an even refilling of the storage container whenever the closable openings jointly open. Since all closable openings are opened simultaneously, pieces of the material will fall through all of the plurality of closable openings and into the storage container below. Thereby, the storage container is refilled evenly. This enables an improved distribution within the storage container and an improved transport of the material out of the storage container by the transport device.

According to an embodiment, the reservoir of the drawer comprises at least one tapered element arranged so that the material in the reservoir moves toward the at least one closable opening. The tapered element is inclined towards the closable opening. Thus, pieces of the material inside the reservoir tend to fall and/or roll and/or slide towards the closable opening. The reservoir of the drawer may comprise a plurality of tapered element arranged at two or more sides of the closable opening. The tapered element reduces the number of pieces of the material left in the reservoir when the closable opening is open. In particular, the bottom of the drawer may substantially consist only of closable openings and of tapered elements. Thus, substantially all pieces of the material will drop through the closable opening, thereby emptying the reservoir when the drawer is in the first position.

According to an embodiment, the storage system comprises a release mechanism configured to open the at least one closable opening when the drawer is moved into the first position, and to close the at least one closable opening when the drawer is moved out of the first position. That release mechanism ensures that the closable opening is only open in the first position of the drawer. In case the drawer is arranged in any other position besides the first position, e.g. in the second position or moving between the two positions, the closable opening will be closed and/or closing. Thus, the material might only fall through the closable opening when the drawer is arranged in the first position.

According to a further development of this embodiment, the release mechanism comprises at least one slidable element configured to:

slide at least partially over the at least one closable opening when the drawer is moved out of the first position, thereby closing the at least one closable opening, and slide at least partially away from the closable opening when the drawer is moved into the first position, thereby opening the at least one closable opening.

In this embodiment, the closable opening may be closed and opened by the slidable element. The slidable element may be provided as a slidable board, tablet, or wall in or at the bottom of the drawer. In particular, the slidable element may be configured as the bottom wall of the drawer. The slidable element may be provided as a substantially flat and plain element, thereby saving space and weight.

The release mechanism may comprise at least one magnet arranged to control the sliding movement of the slidable element of the release mechanism. The at least one magnet may interact with another magnet and/or metal parts of the storage system to close or open the closable opening. Thus, the closable opening may be opened and/or closed by an electromagnetic force.

In a further development of the embodiment, the drawer comprises at least one first magnet arranged to interact with at least one first counter-element of the slidable element so that the slidable element is locked in a state in which the slidable element closes the closable opening when the drawer is in the second position. The slidable element comprises at least one second magnet arranged to interact with at least one second counter-element of the storage system so that the slidable element slides away from the closable opening when the drawer is moved into the first position. When the drawer is moved out of the first position, the at least one second magnet interacts with the at least one second counter-element so that the slidable element slides over the closable opening until the first magnet interacts with the first counter-element, thereby locking the slidable element and the state in which the slidable element closes the closable opening. Both the first magnet and the first counter-element may be arranged at the drawer and/or as elements of the drawer. The first magnet and the first counter-element enable the closable opening to remain in the closed state when the drawer is moved out of the first position. The first magnet and the first counter-element may be arranged adjacent and/or in physical contact with each other when the drawer is not in the first position. The first counter-element may be provided as a metallic and/or magnetic element to interact with the first magnet to provide a magnetic force directed to keep the slidable element arranged over the closable opening.

The second counter-element interacts with the second magnet so that the slidable element slides away from the closable opening and the drawer is moved into the first position. Therein, an attractive or repulsive magnetic force between the second magnet and the second counter-element may ensure that the slidable element opens the closable opening. For this, the magnetic force between the second magnet and the second counter-element exceeds the magnetic force between the first magnet and the first counter-element. Alternatively, the second counter-element may be arranged as a stopper for the slidable element that physically moves the slidable element into an open position when the drawer is moved into the first position. The second counter-element may be arranged so that it does not move with the drawer, but relative to the drawer. For example, the second counter-element may be provided as an element of the storage container and/or be arranged at the storage container to only interact with the second magnet when the slidable element is at least close to the position it is arranged in when the drawer is arranged in the first position.

In an embodiment, an attractive magnetic force may be effective between the second magnet and the second counter-element when the drawer is in the first position. When the drawer is moved out of the first position, the second magnet of the slidable element "sticks" to the second counter-element, thereby forcing the slidable element to keep its position while the rest of the drawer, in particular the frame and/or reservoir of the drawer, is moved out of the first position. At one point, the drawer may be moved so far away from the first position, that the second magnet releases the second counter-element and moves farther away from it. When the second magnet releases the second counter-element, the closable opening is closed by the slidable element.

In this embodiment, the positions of the first magnet and the first counter-element may be swapped, so that one of the first magnet and the first counter-element is arranged at the slidable element and the other one at the frame of the drawer. Also, the position of the second magnet and the second counter-element may be swapped so that one of the second magnet and the second counter-element is arranged at the slidable element and the other one at the storage container. The first magnet and/or the second magnet may be provided as a permanent magnet and/or as an electromagnet. Each of the first and second counter-elements may be provided as a metallic element, as a magnetic element, as a permanent magnet, and/or as an electromagnet.

According to an embodiment, the transport device is configured to retrieve and transport the material at a substantially constant pace, and/or substantially independently of the position of the drawer. This design and configuration of the transport device and the storage system enables refilling of the storage container by opening and closing the drawer without interrupting the transport device and, in particular, without interrupting the supply of material from the storage container. This functionality may be provided by separating the movement and functionality of the drawer from the movement and functionality of the transportation device.

According to an embodiment, the storage system comprises a material sensor (15 in FIG. 1), configured to detect whether a material fill level in the storage container is below a predefined value. An indicator in communication with the material sensor 15 may indicate that the storage container needs a refill. This may be indicated, e.g., visually and/or acoustically. For example, a graphical user interface or a flashing light may be used to indicate to an operator that the storage container needs a refill. The operator may then open the drawer, refill the reservoir in the drawer, and close the drawer back into its first position, thereby refilling the storage container.

According to an embodiment, the storage system comprises an electromagnet operable to lock and/or unlock the drawer in the first position and to release the drawer from the first position. In the locked state, the electromagnet may ensure that the drawer is always closed in its first position and may not be opened. Thus, an accidental and/or unauthorized opening of the drawer may be prevented. The electromagnet may automatically unlock the drawer when a material sensor 15 detects that a material fill level in the storage container is below the predefined value.

According to an embodiment, the drawer and the reservoir are configured to receive sample tube caps in the second position and to drop the sample tube caps through the closable opening into the storage container in the first position. Thus, the storage system may be provided as a push cap feeder and/or as integral part of a tube analysing system, in particular an automated tube analysing system.

According to an embodiment, the drawer is extendable from the storage system and retractable into the storage system via slide rails. The slide rails enable the movability of the drawer between the first position and the second position. The side rails may connect the inside of the storage container with a frame of the drawer.

According to a second aspect of the invention, a method for storing material such as sample tube caps in a storage system comprises the steps:
moving a drawer comprising a reservoir from a first position into a second position,
receiving material into the reservoir of the drawer when the drawer is arranged in the second position,
moving the drawer into the first position where at least one closable opening in the bottom of the reservoir is opened, and
releasing the material through the closable opening into a storage container arranged below the drawer when the drawer is arranged in the first position.

The method may be performed with a storage system according to the first aspect. Thus, all features of the first aspect may be used in the method according to the second aspect.

According to an embodiment, the method comprises the further steps of retrieving material from the storage container and transporting the material out of the storage container by a transport device, wherein the transport device may retrieve and transport the material at a substantially constant pace, and/or substantially independent of the position of the drawer.

BRIEF DESCRIPTION OF THE DRAWINGS

Embodiments of the invention are described with reference to the figures. Features of the embodiments shown in the figures may be combined with alternative embodiments. Reference numbers identify identical or similar features of different embodiments. The embodiments as shown by:

FIG. 1 shows a cross section of a storage system 1. The storage system 1 comprises a storage container 10 provided as substantially cuboid box. The storage container 10 is configured to receive and store material, in particular consumable material such as sample tube caps. The storage container 10 comprises lateral walls that limit a storage space for the material in the lateral directions.

The storage container 10 comprises an inclined bottom 11 that is substantially shaped like a hopper. The inclined bottom 11 comprises at least one lowest portion 12 towards which the inclined bottom 11 is inclined. Thus, material stored in the storage container 10 automatically moves towards the lowest portion 12 driven by gravity. At the lowest portion 12, the material is received by a transport device 30. The transport device 30 comprises a conveyor for conveying the material from the lowest portion 12 out of the storage container 10, e.g. to an access point. Outside of the storage container 10, some pieces of the material may be grabbed and/or used by another machine, e.g. a robot.

In an embodiment, the storage container 10 is used to store sample tube caps. In this embodiment, the transport device 30 receives sample tube caps at the lowest portion 12 of the inclined bottom 11 and transports said sample tube caps out of the storage container 10. Outside of the storage container 10, the sample tube caps may be grabbed by a robot that uses said sample tube caps to close sample tubes.

Figure 1:
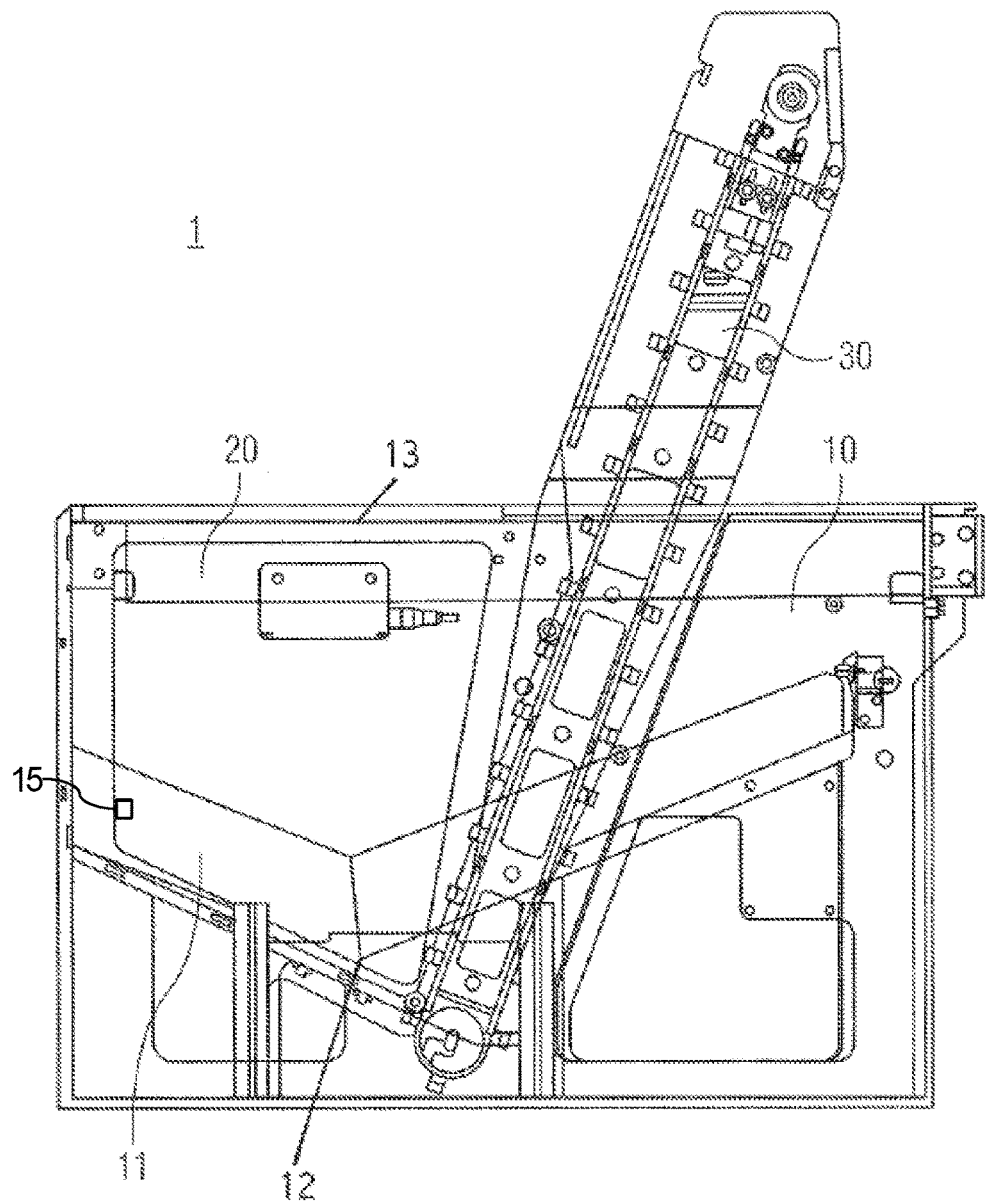
FIG. 1 a cross section of a storage system comprising a drawer.

The storage space provided by the storage container 10 is limited in an upwards direction by a drawer 20 that is shown in FIG. 1 in a first, closed position. In its first, closed position, the drawer 20 is arranged as an upper wall of the storage container 10. The drawer 20 can be moved out of its first position into an extended, second position (not shown in FIG. 1) in which it extends out of the storage container 10. The storage container 10 further comprises an upper wall 13 above the drawer 20 that limits the storage space in an upwards direction.

Figure 2A:
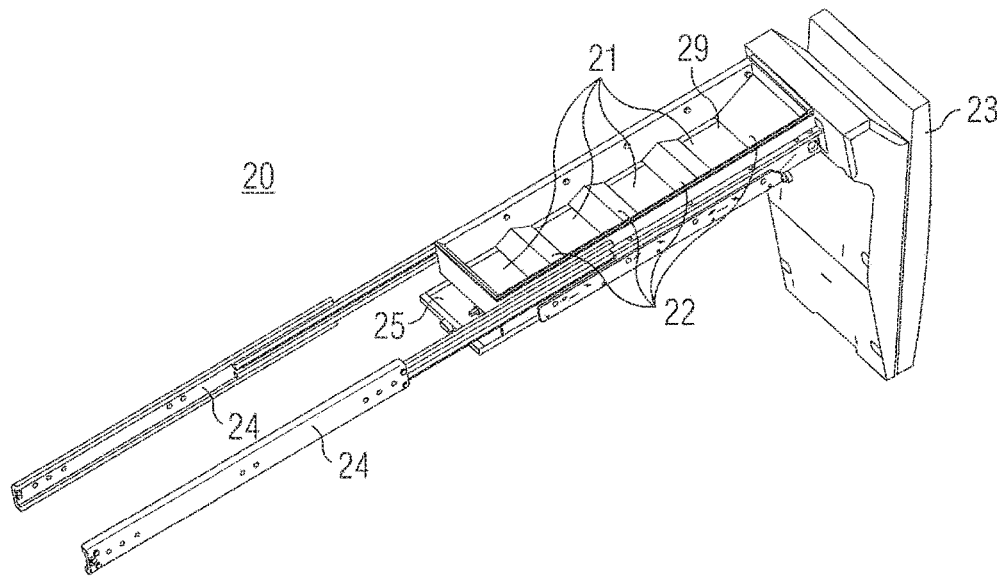
FIG. 2A a perspective view of the drawer in an opened, second position.

FIG. 2A shows a perspective view of the drawer 20 in a second, extended position. The drawer 20 comprises slide rails 24, which connect two opposite sides of the drawer 20 to the inside of the storage container 10 (see FIG. 1). The drawer 20 is configured and designed to be moveable from its first position to its second position and from its second position to its first position in a sliding movement along the slide rails 24.

The drawer 20 comprises a front 23 at a front end of a frame of the drawer. The front 23 is arranged and designed to allow a user to easily operate the drawer and may, e.g., comprise a handle and/or gripping orifice to enable an easy and simple opening and closing of the drawer 20 by a user. When closed, the front 23 may be adjacent to a lateral side of the storage container 10.

As most common drawers, the drawer 20 comprises a reservoir 29 in which material may be arranged. The reservoir 29 comprises no cover so that material may be placed into the reservoir 29 from above when the drawer is arranged in its second position (see FIG. 2A). The reservoir 29 is limited at four lateral sides by walls of the drawer 20. Said four lateral walls include the front 23 and are provided as part of a frame or as the frame of the drawer 20. Furthermore, the drawer 20 comprises a bottom that forms the bottom of the reservoir 29. At the bottom of the drawer 20, at least one closable opening 21 is arranged. In the embodiment shown in FIG. 2A, the drawer comprises a plurality of closable openings 21, in particular four closable openings 21. In the extended position of the drawer 20, namely in its second position shown in FIG. 2A, all closable openings 21 are closed by a slidable element 25. The slidable element 25 may be shaped like a tablet, comprising multiple holes that are not shown in FIG. 2A.

The slidable element 25 is slidable between at least two positions. In one position, the slidable element 25 closes the closeable openings 21. In another position, the slidable element 25 is arranged so that its holes are arranged at the closeable openings 21. Accordingly, the shape and position of the holes may correspond to the shape and position of the closable openings 21. Thus, the closable openings 21 are effectively open (see also FIG. 3A). The slidable element 25 may be designed and arranged to be slidable in a direction parallel to the direction in which the drawer 20 is moved between its first and second position. The sliding element 25 may be slidable in a sliding direction which is parallel to the direction in which the sliding rails 24 extend.

At the bottom of the reservoir 29 and/or above the slidable element 25, one or more tapered elements 22 may be arranged. In the embodiment shown in FIG. 2A, the drawer 20 comprises a plurality of tapered elements 22, e.g. four tapered elements 22, some of which are arranged between two closable openings 21. Each tapered element 22 provides at least one inclined plane that is inclined towards one of the closable openings 22. Some or all of the tapered elements 22 may be provided as two-sided tapered elements comprising two inclined planes that are inclined towards two adjacent closable openings 21. Furthermore, the drawer 20 may comprise one or two one-sided tapered elements comprising only one inclined plane. Such a one-sided tapered element may be arranged at one or both ends of the drawer 20 that limit the reservoir in the sliding direction. The one-sided tapered element may be arranged adjacent to only one closable opening 21.

The slidable element 25 may be arranged and/or configured to slide from a blocking position, wherein the slidable element 25 is blocking one or more of the closable opening (s) 21 at the bottom of the reservoir 29, to a releasing position, wherein the slidable element 25 is no longer blocking said closable opening(s) 21, by sliding under one or more of the tapered element(s) 22 which is adjacent to said closable opening(s) 21.

In the embodiment shown in FIG. 2A, the bottom of the drawer 20 substantially consists of closable openings 21 and tapered elements 22. Therein, the closable openings 21 are arranged between the tapered elements 22. Also, the tapered elements 22 are arranged between the closable openings 21. Thus, because the closable openings 21 are closed, the material within the reservoir 29 rests either upon one of the closable openings 21 or upon one of the tapered elements 22. When the closable openings 21 are opened (see FIG. 3A), the material resting upon the closable openings 21 will fall through the closable openings 21 and into the storage container 10. The material resting upon the tapered elements 22 will slide along the inclined planes of the tapered elements 22 towards one of the adjacent closable openings 21 and, since all closable openings 21 are opened, fall through one of said openings and into the storage container 10. Thus, the tapered elements 22 may ensure that the reservoir 29 is completely emptied out into the storage container 10 when the closable openings 21 are open. The tapered elements 22 and the closable openings 21 may be arranged so that not even a single piece of the material remains in the reservoir 29 when the closable openings are opened.

Figure 2B:
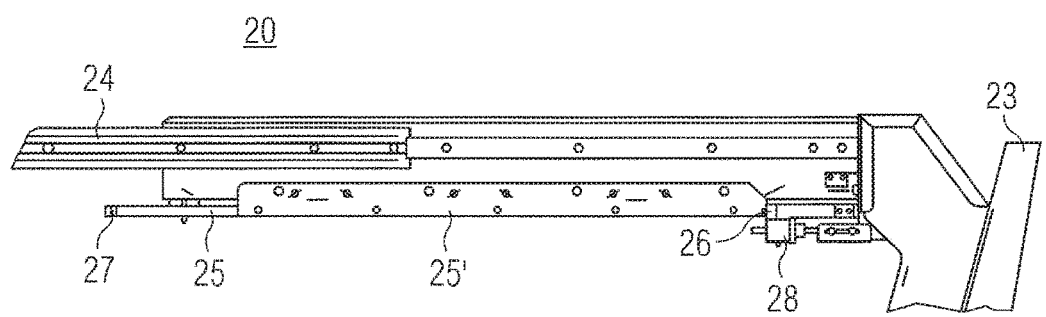
FIG. 2B a side view of the drawer in an opened, second position.

FIG. 2B shows a side view of the drawer 20 in its second, opened, and extended position. In this position, the slidable element 25 closes all of the closable openings 21. At a front end of the drawer 20, namely in the vicinity of the front 23, a first magnet 26 is arranged to ensure that the slidable element 25 stays in the position wherein it closes the closable openings 21. The first magnet 26 ensures that the closable openings 21 will be kept closed when the reservoir 29 is refilled. The first magnet 26 may be arranged at the frame of the drawer 20 and interact with a corresponding counterpart, e.g. a first counter-element, arranged at the slidable element 25. In an alternative embodiment, the first magnet 26 may be arranged at the slidable element 25 and interact with a portion of the frame of the drawer and/or the first counter-element of the drawer arranged at the frame of the drawer 20.

At the front end of the drawer 20, namely at the end of the drawer 20 at which the front 23 is arranged, an electromagnet 28 is arranged. The electromagnet 28 may be controlled by a controller that controls electromagnet 28 such that it is magnetic as long as the drawer 20 is in its first position, namely its closed position (see, e.g., FIG. 3B). The controller may be implemented, e.g., as a software controlled controller. When the drawer 20 is in its first position, the electromagnet 28 is powered so that that the drawer 20 may not be opened. This prevents the drawer 20 from being accidentally opened. The controller may be configured to drive electromagnet 28 so that it only releases the drawer 20 when a fill level within the storage container 10 is below a predetermined threshold and/or when it is released by a user.

The first magnet 26 is arranged to ensure that the slidable element 25 does not accidentally open the closeable openings 21. Therefore, the drawer 20 may comprise two or more first magnets 26 arranged at a front end of the drawer, adjacent to the front 23, at a left and/or at a right side of the drawer 20. The first magnet 26 may be arranged at a frame of the drawer 20 and interact with a counterpart, e.g. a metallic, a magnetic and/or ferromagnetic counterpart, arranged at the front end of the slidable element 25.

Figure 3A:
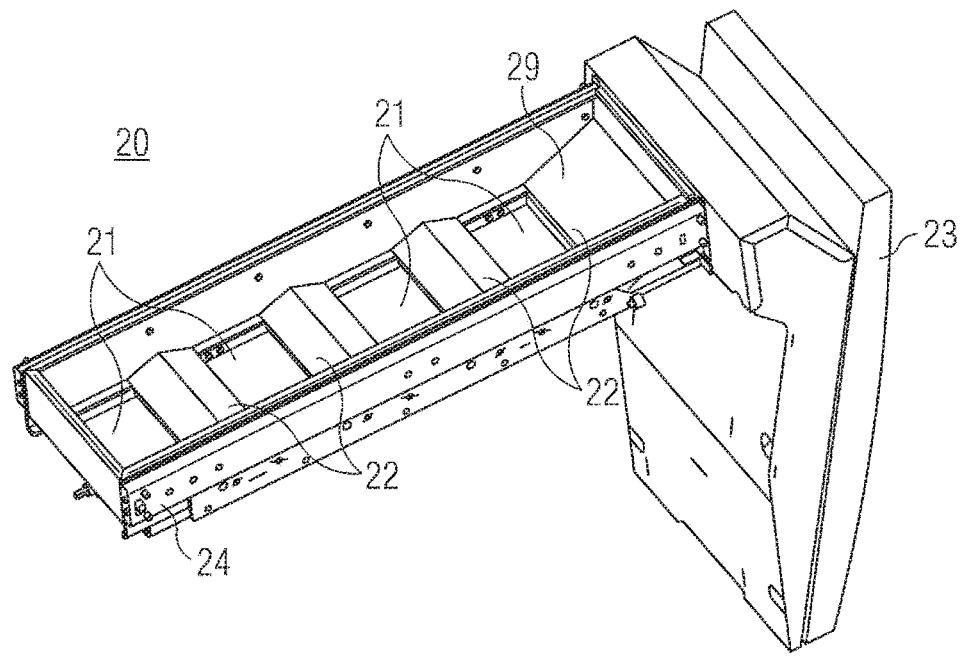
FIG. 3A a perspective view of the drawer in a closed, first position.
Figure 3B:
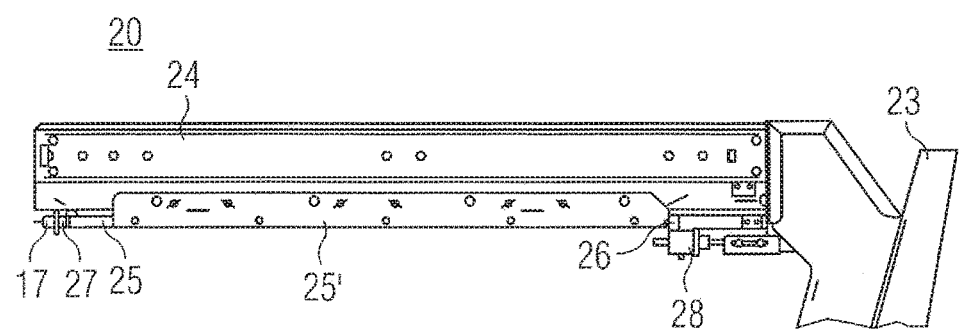
FIG. 3B a side view of the drawer in a closed, first position.

The slidable element 25 may be held within a guiderail 25' so that it may slide within the guiderail 25' between a closed position (see FIG. 2B) and an opened position (see FIG. 3B). The guide rail 25' may be fixed to the frame of the drawer 20. At a back end of the drawer, namely at an end that is opposed to the front 23, at least one second magnet 27 is arranged at the slidable element 25. At said back end, two or more second magnets 27 may be arranged.

FIG. 3A shows a perspective view of the drawer 20 in its first position. In said first position, the drawer 20 is closed and pushed into the storage container 10. In the first position of the drawer 20, the closable openings 21 are open. Thus, as described above, the material arranged in the reservoir 29 may drop through the closable openings 21 into the storage container 10.

In the first position of the drawer, the slidable element 25 is in a different position relative to the frame of the drawer 20 than when the drawer 20 is its second position.

FIG. 3B shows a side view of the drawer 20 in its first position. As shown in FIG. 3B, in particular in comparison with FIG. 2B, the slidable element 25 is arranged in a position closer to the front 23 of the drawer 20. When the drawer is moved from its second position (as shown in FIG. 2B) into its first position, the slidable element 25 moves together with the frame of the drawer 20 (held by the first magnet 26) until it contacts a second counter-element 17 with its second magnets 27. The second counter-element 17 may be arranged inside of the storage container 10. The second counter-element 17 is designed and arranged to form a stop impeding any further movement of the backside of the slidable element 25 into the storage container 10. However, the frame of the drawer 20, the guiderail 25', and the reservoir 29 may be pushed into the storage container 10 further than the slidable element 25. Thus, the slidable element 25 is pushed—relative to the guiderail 25'—towards the front 23. Since the guiderail 25' is fixed to the frame of a drawer 20, the slidable element 25 moves relative to the frame of the drawer 20 and, in particular, relative to the closable openings 21. The slidable element 25 moves relative of the closable openings 21 until the position of its holes correspond to the position of the closable openings 21. Thus, the closable openings 21 are opened.

The storage container 10 comprises as many second counter-elements 17 as the drawer 20 comprises second magnets 27. The second counter-elements 17 may be metallic, ferromagnetic, and/or magnetic. Furthermore, the second counter-element 17 may be provided with a suspension to cushion the slidable movement of the drawer 20 into the storage container 10. Also, the slidable element 25 may be provided with a suspension to cushion the sliding movement of the slidable element 25 relative to the drawer 20, e.g., within guiderails 25'.

When the drawer 20 is pulled out of its first position (as shown in FIG. 3B) and towards its second position (as shown in FIG. 2B), a magnetic force between the second magnets 27 and the second counter-elements 17 pull the slidable element 25 out of its opened position and in a direction away from the front 23. Thereby, the closable openings 21 are closed. In this position, the first magnets 26 may ensure that the slidable element 25 is fixed in its closed state.

In an alternative embodiment, the second counter-elements 17 may be provided as magnets and the second magnets 27 may be provided as counter-elements thereof. Thus, the second magnets may either be arranged at the end of the slidable element 25 that is opposed to the front 23 or as buffer at the storage container 10, as shown in FIG. 3B with the reference sign 17.

The storage system 1 as shown in FIG. 1 may be configured so that the transport device 30 may be driven substantially independent of the position of the drawer 20. Thereby, the transport device 30 may provide a substantially constant supply of material, e.g., of sample tube caps, even when the drawer 20 is opened for a refill.

The storage container 10 may be configured and/or arranged to store any consumable material, namely material that is frequently required and/or "consumed" in an automatic system.

LIST OF REFERENCE NUMERALS

1 storage system
10 storage container
11 inclined bottom
12 lowest portion
13 upper wall
17 second counter-element
20 drawer
21 closable opening
22 tapered element
23 front
24 slide rail
25 slidable element
25' guide rail
26 first magnet
27 second magnet
28 electromagnet
29 reservoir
30 transport device

What is claimed is:

1. A storage system for storing material, comprising:
a drawer comprising a reservoir, the drawer being movable between a first position and a second position,
a storage container arranged below the reservoir of the drawer when the drawer is arranged in the first position,
a transport device configured to retrieve material from the storage container and to transport the material out of the storage container at a substantially constant pace,
wherein the reservoir of the drawer comprises a bottom comprising a plurality of closable openings which are jointly operable in that
the plurality of closable openings are jointly opened when the drawer is moved from the second position into the first position and
the plurality of closable openings are jointly closed when the drawer is moved from the first position into the second position.

2. The storage system according to claim 1, wherein the closable openings are substantially evenly distributed in the bottom of the reservoir of the drawer.

3. The storage system according to claim 1, wherein the transport device is configured to retrieve and transport the material substantially independent of the position of the drawer.

4. A storage system for storing material, comprising:
a drawer comprising a reservoir, the drawer being movable between a first position and a second position,
a storage container arranged below the reservoir of the drawer when the drawer is arranged in the first position, and
a transport device configured to retrieve material from the storage container and to transport the material out of the storage container at a substantially constant pace,
wherein the reservoir of the drawer comprises a bottom with at least one closable opening, and wherein the reservoir of the drawer comprises at least one tapered element arranged so that material in the reservoir moves toward the at least one closable opening.

5. The storage system according to claim 4, wherein the transport device is configured to retrieve and transport the material substantially independent of the position of the drawer.

6. The storage system according to claim 4, wherein the drawer and the reservoir are configured to receive sample tube caps in the second position and to drop the sample tube caps through the closable opening into the storage container in the first position.

7. A storage system for storing material, comprising:
a drawer comprising a reservoir, the drawer being movable between a first position and a second position, wherein the reservoir of the drawer comprises a bottom with at least one closable opening;
a storage container arranged below the reservoir of the drawer when the drawer is arranged in the first position,
a transport device configured to retrieve material from the storage container and to transport the material out of the storage container at a substantially constant pace, and a release mechanism configured to:
open the at least one closable opening when the drawer is moved into the first position, and
close the at least one closable opening when the drawer is moved out of the first position.

8. The storage system according to claim 7, wherein the release mechanism comprises at least one slidable element configured to:
slide at least partially over the at least one closable opening when the drawer is moved out of the first position, thereby closing the at least one closable opening, and
slide at least partially away from the closable opening when the drawer is moved into the first position, thereby opening the at least one closable opening.

9. The storage system according to claim 8, wherein the release mechanism comprises at least one magnet arranged to control the sliding movement of the slidable element of the release mechanism.

10. The storage system according to claim 8, wherein the drawer comprises at least one first magnet arranged to interact with at least one first counter-element of the slidable element so that the slidable element is locked in a state in which the slidable element closes the closable opening when the drawer is in the second position, the slidable element comprises at least one second magnet arranged to interact with at least one second counter-element of the storage system so that the slidable element slides away from the closable opening when the drawer is moved into the first position, and when the drawer is moved out of the first position, the at least one second magnet interacts with the at least one second counter-element so that the slidable element slides over the closable opening until the first magnet interacts with the first counter-element, thereby locking the slidable element in the state in which the slidable element closes the closable opening.

11. The storage system according to claim 7, wherein the transport device is configured to retrieve and transport the material substantially independent of the position of the drawer.

12. The storage system according to claim 7, comprising a material sensor configured to detect whether a material fill level in the storage container is below a predefined value.

13. The storage system according to claim 7, wherein the drawer and the reservoir are configured to receive sample tube caps in the second position and to drop the sample tube caps through the closable opening into the storage container in the first position.

14. The storage system of claim 7, wherein the material comprises sample tube caps.

15. A method for storing material in a storage system, comprising the steps:

moving a drawer comprising a reservoir from a first position into a second position, receiving material into the reservoir of the drawer when the drawer is arranged in the second position, moving the drawer into the first position where at least one closable opening in a bottom of the reservoir is opened, releasing the material through the closable opening into a storage container arranged below the drawer when the drawer is arranged in the first position, and retrieving material from the storage container and transporting the material out of the storage container by a transport device at a substantially constant pace.

16. The method for storing material according to claim 15, wherein the transport device may retrieve and transport the material substantially independent of the position of the drawer.

17. The method of claim 15, wherein the material comprises sample tube caps.

18. A storage system for storing material, comprising:

a drawer comprising a reservoir, the drawer being movable between a first position and a second position, wherein the reservoir of the drawer comprises a bottom with at least one closable opening, a storage container arranged below the reservoir of the drawer when the drawer is arranged in the first position, a transport device configured to retrieve material from the storage container and to transport the material out of the storage container at a substantially constant pace, and an electromagnet operable to lock the drawer in the first position and to release the drawer from the first position.

19. The storage system according to claim 18, wherein the transport device is configured to retrieve and transport the material substantially independent of the position of the drawer.

20. The storage system according to claim 18, wherein, when the drawer is arranged in the first position, the at least one closable opening is open so that material drops from the reservoir into the storage container, and/or wherein, when the drawer is arranged in the second position, the at least one closable opening is closed so that the reservoir is configured to receive material.

* * * * *